United States Patent
Joo et al.

(10) Patent No.: US 9,624,448 B2
(45) Date of Patent: Apr. 18, 2017

(54) METHOD FOR PREPARING STABILIZED HYDROCARBON OIL BLEND

(71) Applicants: SK Innovation Co., Ltd., Seoul (KR); SK Energy Co., Ltd., Seoul (KR)

(72) Inventors: Chang Woo Joo, Daejeon (KR); Yun Hee Lee, Daejeon (KR); Ki Seok Choi, Daegu (KR); Gwang Hyoun Kim, Daejeon (KR); Young Suk Kim, Seoul (KR); Myoung Han No, Daejeon (KR); Dong Wook Park, Daejeon (KR); Eun Kyoung Kim, Daejeon (KR)

(73) Assignees: SK INNOVATION CO., LTD., Seoul (KR); SK ENERGY CO., LTD., Seoul (KR)

( * ) Notice: Subject to any disclaimer, the term of this patent is extended or adjusted under 35 U.S.C. 154(b) by 224 days.

(21) Appl. No.: 14/395,417

(22) PCT Filed: Apr. 16, 2013

(86) PCT No.: PCT/KR2013/003167
§ 371 (c)(1),
(2) Date: Oct. 17, 2014

(87) PCT Pub. No.: WO2013/157803
PCT Pub. Date: Oct. 24, 2013

(65) Prior Publication Data
US 2015/0090631 A1    Apr. 2, 2015

(51) Int. Cl.
*C10L 1/04* (2006.01)
*G01N 33/28* (2006.01)

(52) U.S. Cl.
CPC ............. *C10L 1/04* (2013.01); *G01N 33/28* (2013.01); *C10G 2300/20* (2013.01); *C10G 2300/302* (2013.01); *C10G 2300/304* (2013.01); *C10G 2300/308* (2013.01); *C10L 2200/0407* (2013.01); *C10L 2290/24* (2013.01); *C10L 2290/60* (2013.01)

(58) Field of Classification Search
CPC .................. C10L 2290/24; C10L 2290/60
See application file for complete search history.

(56) References Cited

U.S. PATENT DOCUMENTS

| | | | |
|---|---|---|---|
| 5,871,634 A | 2/1999 | Wiehe et al. | |
| 7,029,570 B2 | 4/2006 | Mason et al. | |
| 7,618,822 B2 | 11/2009 | Nemana et al. | |
| 8,017,910 B2* | 9/2011 | Sharpe | G01N 21/359 250/253 |

FOREIGN PATENT DOCUMENTS

| | | |
|---|---|---|
| KR | 10-2011-0086706 A | 7/2011 |
| WO | WO 2004/033602 A1 * | 4/2004 |
| WO | 2004033602 A1 | 10/2004 |
| WO | 2004099349 A1 | 11/2004 |

OTHER PUBLICATIONS

International Search Report for PCT/KR2013/003167 dated Jul. 1, 2013 (4 pages).
Magin Lapuerta et al.., "Stability of diesel-bioethanol blends for use in diesel engines," FUEL, 86:1351-1357 (Jan. 3, 2007).
Harry N. Giles, "Methods for Assessing Stability and Cleanliness of Liquid Fuels," Petroleum Products, pp. 108-118 (2003).
L. Molder et al., "Viscosity and Stability of Distillate Petroleum Oil—Residual Petroleum Oil and Distillate Petroleum Oil—Shale Oil Binary Blends," Oil Shale, 16(3):239-248 (1999).
Supplementary European Search Report, EP 13778385.8, Nov. 26, 2015 (8 pages).

* cited by examiner

*Primary Examiner* — Randy Boyer
(74) *Attorney, Agent, or Firm* — Abelman, Frayne & Schwab (57) ABSTRACT

Disclosed herein are a method of preparing a hydrocarbon oil blend having superior storage stability using a novel stability prediction model that is quick, easy and reliable; and a method of predicting the stability of a hydrocarbon blend.

20 Claims, 4 Drawing Sheets

| Classification | Excess O2(%) | | | | |
|---|---|---|---|---|---|
| | 1 | 2 | 3 | 4 | 5 |
| Ignition | 0 | 0 | 0 | 0 | 0 |
| Combustion image | Not taken | | | | |

FIG. 5A

Full Load · Idling

FIG. 5B

Full Lord · Idling · Full Lord

METHOD FOR PREPARING STABILIZED HYDROCARBON OIL BLEND

RELATED APPLICATIONS

This application is a United States national phase application under 35 USC §371 of PCT/KR2013/003167 filed on Apr. 16, 2013, and claims the benefit under 35 USC §119 of Korean patent application number KR 10-2012-0039871 filed Apr. 17, 2012, the disclosures of which are incorporated herein by reference in their entireties.

TECHNICAL FIELD

The present disclosure relates to a method of preparing a stabilized hydrocarbon oil blend. More particularly, the present disclosure relates to a method of preparing a hydrocarbon oil blend having superior storage stability using a novel stability prediction model that is quick, easy and reliable, and to a method of predicting the stability of a hydrocarbon blend.

BACKGROUND ART

With the increasing depletion of petroleum resources, there are needs for methods of decreasing the material costs and producing value-added products using heavy oils generated in the course of refining crude oils or using, as alternatives to crude oils, inexpensive heavy hydrocarbon oils such as bitumen. In order to actively address these environmental changes in the petroleum product fields, a variety of heavy oils are blended as semi-finished heavy oil products and thus utilized for fuel oils, ship oils and the like. Also, crude oils derived from various origins have been employed via blending. Since blending of hydrocarbon oils or crude oils is typically implemented in the oil refining fields, stabilized hydrocarbon oil blends have to be essentially produced.

However, such heavy oils and crude oils contain a considerable amount of asphaltenes, and thus stability thereof may become problematic upon blending. Individual heavy oils or crude oils are composed primarily of saturated hydrocarbons (saturates), aromatic hydrocarbons (aromatics), resins (mainly including alkyls and naphthenoaromatic hydrocarbons) and asphaltenes, wherein asphaltenes and maltenes (i.e., saturated hydrocarbons, aromatic hydrocarbons and resins) are linked in the form of micelles to form a colloidal system in a dispersion phase, and are thus stabilized.

In this regard, saturated hydrocarbons have the lowest polarity, and molecular weight, polarity and aromaticity are increased in the order of aromatic hydrocarbons, resins and asphaltenes. As such, asphaltenes are insoluble in n-heptane (C7 insoluble), and maltenes are soluble in n-heptane. Typically, asphaltene content is measured by ASTM D 6560-00. The exemplary properties of asphaltenes are shown in Table 1 below.

TABLE 1

| | Properties |
|---|---|
| H/C ratio | 0.8-1.4 |
| Mw | Monomer: about 500-1000 |
| | Micelle: 1000-5000 |
| Heteroatom content | Sulfur (S): 0.5-10 wt % |
| | Nitrogen (N): 0.6-2.6 wt % |
| | Oxygen (O): 0.3-4.8 wt % |
| Contained metal | Nickel, Vanadium, Iron, etc. |

Among the four types of hydrocarbons as above, asphaltenes having the highest C/H ratio are configured such that condensed polycyclic aromatics are stacked in the form of a multilayer, and are sensitive to thermal or chemical reactions or blending. Hence, asphaltenes are regarded as an important factor that affects storage stability of the blend. When storage stability is good, asphaltenes may adsorb resins from maltenes to form micelles, and are three-dimensionally (spatially) stabilized in an adsorption equilibrium state and do not settle in oils.

However, when resins are separated from asphaltenes due to deviation of adsorption equilibrium via the blending of different oils, asphaltenes may be settled (precipitated) (referred to as "dry sludge" or "total sediments").

Even if the particular oils exhibit stabilized behaviors when they are individually present, the stability of asphaltenes therein may be significantly influenced by the changes of conditions such as blending with different types of oils.

When heavy oils or heavy oil and crude oil are blended so as to be utilized as fuel oils or ship oils or when various crude oils are blended so as to be transported via pipelines or to serve as fuel oils, the precipitation of asphaltenes arising from blending of hydrocarbon oils may cause serious problems including nozzle plugging in combustion devices, fouling and coking, and clogging of pipelines.

In this regard, methods of pre-checking stability problems of the hydrocarbon oils or crude oils have been devised in the pertinent art. For example, SPOT testing according to ASTM D 4740-02 is used to evaluate storage stability by qualitatively measuring cleanliness of oils and compatibility (miscibility) of components (semi-finished products) to be blended, and HFT (Hot Filtration Test) according to ASTM D 4870-99 is a quantitative method for measuring the total precipitate in oils.

Moreover, a method of evaluating the extent of potential deterioration of stability by measuring the amount of saturated hydrocarbons relative to aromatic compounds (which is referred to as "SARA") is known. In addition, the use of sensitive neutron scattering to measure the presence and amount of asphaltene aggregates in petroleum oil blends (U.S. Pat. No. 7,029,570) is known in the art.

Although such methods are useful for checking the stability of the blends in part, they have technical limitations, for example, how to blend a plurality of hydrocarbon oils without precipitation of asphaltenes cannot be predicted in advance.

With the aim of solving such technical limitations, a method of preparing a stabilized blend of two or more petroleum oils using new parameters including $I_N$ (Insolubility Number) and $S_{BN}$ (Solubility Blending Number) is disclosed (U.S. Pat. No. 5,871,634). Also, a method of predicting stability of an oil blend using parameters such as critical solvent power and solvent power for individual oils is disclosed (U.S. Pat. No. 7,618,822).

However, the aforementioned techniques involve comparatively complicated calculations and procedures to determine the related parameters, and thus a method of preparing a stabilized hydrocarbon oil blend using a prediction model that is quick, easy and reliable is still needed in the art.

DISCLOSURE

Technical Problem

Accordingly, embodiments of the present disclosure are intended to provide a method of quickly, easily and reliably predicting stability of a blend, and a method of preparing a stabilized hydrocarbon oil blend using the same.

Technical Solution

A first aspect provides a method of preparing a hydrocarbon blend by blending at least two hydrocarbon oils, comprising:

determining a stability factor of each of the at least two hydrocarbon oils; and blending the at least two hydrocarbon oils so as to satisfy Mathematical Formula 1 below based on the determined stability factor:

$$\sum_{i=1}^{n} a_i A_i > 0 \quad \text{[Mathematical Formula 1]}$$

wherein $a_i$ is a stability factor of a hydrocarbon oil (i) in the blend, $A_i$ is wt % of the hydrocarbon oil (i) in the blend, and n indicates the number of hydrocarbon oils in the blend and is an integer of 2 or more, (a) when a SPOT value of a hydrocarbon oil according to ASTM D 4740-02 is less than 2, the stability factor is determined by Mathematical Formula 2 below:

$$\text{Stability Factor}(a_i) = 1 \times B_i^{-1} \quad \text{[Mathematical Formula 2]}$$

wherein $B_i$ is a minimum amount of the hydrocarbon oil (i) to be blended with 100 g of a reference sample having SPOT 5 so as to exhibit SPOT 1, and (b) when a SPOT value of a hydrocarbon oil according to ASTM D 4740-02 is 2 or more, the stability factor is determined by Mathematical Formula 4 below:

$$\text{Stability Factor}(a_i) = -(0.025 \times T_i \times 0.01) \quad \text{[Mathematical Formula 4]}$$

wherein $T_i$ is a minimum amount of toluene to be blended with 100 g of the hydrocarbon oil (i) so as to exhibit SPOT 1.

A second aspect provides a method of preparing a hydrocarbon blend by blending at least two hydrocarbon oils, comprising:

determining a stability factor of each of the at least two hydrocarbon oils; and blending the at least two hydrocarbon oils so as to satisfy Mathematical Formula 1 below based on the determined stability factor:

$$\sum_{i=1}^{n} a_i A_i > 0 \quad \text{[Mathematical Formula 1]}$$

wherein $a_i$ is a stability factor of a hydrocarbon oil (i) in the blend, $A_i$ is wt % of the hydrocarbon oil (i) in the blend, and n indicates the number of hydrocarbon oils in the blend and is an integer of 2 or more, (a) when a SPOT value of a hydrocarbon oil according to ASTM D 4740-02 is less than 2, the stability factor is determined by Mathematical Formula 3 below:

$$\text{Stability Factor}(a_i) = 1 \times C_i^{-1} \times 0.828 \quad \text{[Mathematical Formula 3]}$$

wherein $C_i$ is a minimum amount of the hydrocarbon oil (i) to be blended with 100 g of a reference sample having SPOT 4 so as to exhibit SPOT 1, and (b) when a SPOT value of a hydrocarbon oil according to ASTM D 4740-02 is 2 or more, the stability factor is determined by Mathematical Formula 4 below:

$$\text{Stability Factor}(a_i) = -(0.025 \times T_i \times 0.01) \quad \text{[Mathematical Formula 4]}$$

wherein $T_i$ is a minimum amount of toluene to be blended with 100 g of the hydrocarbon oil (i) so as to exhibit SPOT 1.

A third aspect provides a method of predicting stability of a blend of at least two hydrocarbon oils, comprising:

determining a stability factor of each of the at least two hydrocarbon oils to be blended; and determining stability depending on whether the blend of the hydrocarbon oils satisfies Mathematical Formula 1 below based on the determined stability factor:

$$\sum_{i=1}^{n} a_i A_i > 0 \quad \text{[Mathematical Formula 1]}$$

wherein $a_i$ is a stability factor of a hydrocarbon oil (i) in the blend, $A_i$ is wt % of the hydrocarbon oil (i) in the blend, and n indicates the number of hydrocarbon oils in the blend and is an integer of 2 or more, (a) when a SPOT value of a hydrocarbon oil according to ASTM D 4740-02 is less than 2, the stability factor is determined by Mathematical Formula 2 below:

$$\text{Stability Factor}(a_i) = 1 \times B_i^{-1} \quad \text{[Mathematical Formula 2]}$$

wherein $B_i$ is a minimum amount of the hydrocarbon oil (i) to be blended with 100 g of a reference sample having SPOT 5 so as to exhibit SPOT 1, and (b) when a SPOT value of a hydrocarbon oil according to ASTM D 4740-02 is 2 or more, the stability factor is determined by Mathematical Formula 4 below:

$$\text{Stability Factor}(a_i) = -(0.025 \times T_i \times 0.01) \quad \text{[Mathematical Formula 4]}$$

wherein $T_i$ is a minimum amount of toluene to be blended with 100 g of the hydrocarbon oil (i) so as to exhibit SPOT 1.

A fourth aspect provides a method of predicting stability of a blend of at least two hydrocarbon oils, comprising:

determining a stability factor of each of the at least two hydrocarbon oils to be blended; and determining stability depending on whether the blend of the hydrocarbon oils satisfies Mathematical Formula 1 below based on the determined stability factor:

$$\sum_{i=1}^{n} a_i A_i > 0 \quad \text{[Mathematical Formula 1]}$$

wherein $a_i$ is a stability factor of a hydrocarbon oil (i) in the blend, $A_i$ is wt % of the hydrocarbon oil (i) in the blend, and n indicates the number of hydrocarbon oils in the blend and is an integer of 2 or more, (a) when a SPOT value of a hydrocarbon oil according to ASTM D 4740-02 is less than 2, the stability factor is determined by Mathematical Formula 3 below:

$$\text{Stability Factor}(a_i) = 1 \times C_i^{-1} \times 0.828 \quad \text{[Mathematical Formula 3]}$$

wherein $C_i$ is a minimum amount of the hydrocarbon oil (i) to be blended with 100 g of a reference sample having SPOT 4 so as to exhibit SPOT 1, and (b) when a SPOT value of a hydrocarbon oil according to ASTM D 4740-02 is 2 or more, the stability factor is determined by Mathematical Formula 4 below:

$$\text{Stability Factor}(a_i) = -(0.025 \times T_i \times 0.01) \quad \text{[Mathematical Formula 4]}$$

wherein $T_i$ is a minimum amount of toluene to be blended with 100 g of the hydrocarbon oil (i) so as to exhibit SPOT 1.

Advantageous Effects

According to embodiments of the present disclosure, a method of preparing a stabilized hydrocarbon oil blend can employ a quick, easy and reliable model able to predict stability of the blend, and the stability factor of each of two or more hydrocarbon oils to be blended can be arranged into a database in advance, thereby enabling rapid checking of the stability of the blend before actual blending.

Particularly, the kinds and amounts of hydrocarbon oils to be blended are adjusted so as to satisfy requirements in accordance with particular Mathematical Formulae based on the stability factors, thereby simplifying preparation of a stabilized hydrocarbon oil blend. Therefore, a wide range of commercial uses are expected in future.

MODE FOR INVENTION

The present disclosure may be embodied by the following description. The following description is to be understood as disclosing preferred embodiments, and the present invention is not necessarily limited thereto. Furthermore, the appended drawings are used to understand embodiments of the present disclosure and are not construed as limiting the present invention.

Hydrocarbon Oils

Methods according to embodiments of the present disclosure may be applied to various hydrocarbon oils that may cause instability due to the precipitation of asphaltene upon blending with other hydrocarbons. In particular, such methods may be applied to crude oils or hydrocarbon oils produced in the oil refining processes. When many of the hydrocarbon oils as stated above exist individually, they can be relatively stable with an appropriate balance maintained between asphaltene and maltene. Furthermore, since asphaltene is composed of polar polycyclic aromatic, an aromatic component may function as a kind of solvent. Thus, the hydrocarbon oils tend to be more stable, as the aromatic content therein is higher.

Also, the stability of asphaltene may be affected by the properties of aromatics in the hydrocarbon oils. For example, when the substituent (e.g. alkyl substituent) of aromatics is bulky, the asphaltene solubility may become good. In contrast, when the substituent of aromatics is not bulky, the asphaltene solubility may comparatively decrease. However, when the hydrocarbon oils, which are individually in a stable state, are blended with other hydrocarbon oils, it is noted that a phenomenon where asphaltene in the blend, not stably present in maltene, may be caused. Usable in this embodiment, the asphaltene content in hydrocarbon oils may be, for example, about 15 wt % or less, and particularly about 7 wt % or less, but the present invention is not limited thereto.

As hydrocarbon oils, heavy oil fractions produced in the oil refining process may be typically used. As such, heavy oil fractions may have the gravity of about 0.8 to 1.2, and particularly about 0.84 to 1 (ASTM D1298).

Also, a blend may be prepared by combining a crude oil with a heavy oil. The use of light oils is not excluded, but inexpensive heavy oils that cause stability to remarkably deteriorate due to asphaltene may be advantageously applied in a certain embodiment.

In an exemplary embodiment, taking into consideration the end use (especially fuel oil) of blends to be produced, hydrocarbon oils may have a sulfur content (ASTM D4294) of about 5 wt % or less (particularly about 4 wt % or less), a viscosity (ASTM D445/ASTM D2270) of about 1 to 1500 mm$^2$/s (particularly about 2 to 1300 mm$^2$/s), a flash point (ASTM D92) of at least about 30° C. (particularly about 35 to 220° C.), and a pour point (ASTM D97) of about 40° C. or less (particularly about 35° C. or less).

Also, the hydrocarbon oils may have a nitrogen content of, for example, about 5000 ppm or less, and particularly about 3500 ppm or less, and CCR (Conradson Carbon Residue; ASTM D4530) of about 15 wt % or less, and particularly about 12 wt % or less.

The ranges of the properties as above are merely illustrative, and it should be understood that the present invention is not necessarily limited to specific numerical ranges.

The oils and the related properties usable in the exemplified embodiment of the present disclosure are shown in Table 2 below.

TABLE 2

| | Properties | | | | | |
|---|---|---|---|---|---|---|
| Sample | Gravity (15/4° C.) | Flash point (° C.) | Viscosity (mm$^2$/s) | Sulfur (wt %) | Pour point (° C.) | SPOT |
| LCO | 1.0255 | 152 | 6 | 0.92 | −7.5 | 1 |
| HCN | 0.9304 | 67 | 2 | 0.35 | <−45.0 | 1 |
| SLO | 1.0837 | 86 | 88 | 1.14 | −2.5 | 1 |
| H/S AR | 0.9814 | 194 | 1,237 | 3.76 | 12.5 | 1 |
| L/S AR | 0.9441 | 178 | 531 | 0.26 | 35.0 | 1 |
| t-LGO | 0.8438 | 78 | 4 | 0.00 | 0.0 | 1 |
| RHDS t-AR | 0.9267 | 220 | 186 | 0.32 | 10.0 | 3 |
| VRDS t-AR | 0.9273 | 84 | 213 | 0.29 | 27.5 | 5 |

LCO: light cycle oil
HCN: heavy catalytic cracked naphtha
SLO: slurry oil
H/S AR: high sulfur atmospheric residue
L/S AR: low sulfur atmospheric residue
t-LGO: treated light gas oil
RHDS t-AR: residue hydrodesulfurization treated atmospheric residue
VRDS t-AR: vacuum residue desulfurization treated atmospheric residue Among the hydrocarbon oils shown in Table 1, VRDS t-AR having SPOT 5 is very unstable and contains a considerable amount of asphaltene aggregates, and thus tens to deteriorate the stability of blends with the other hydrocarbon oils.

As used herein, crude oils are not limited to those derived from specific origins but crude oils having various properties may be used. The properties of exemplary crude oils are shown in Table 3 below.

TABLE 3

| Crude oil | Gravity (15/4° C.) | Sulfur (wt %) | Viscosity (mm$^2$/s) | Flash point (° C.) | Pour point (° C.) | Nitrogen (ppm) | CCR (wt %) | SPOT |
|---|---|---|---|---|---|---|---|---|
| PYR[1] | 0.9390 | 0.19 | 44 | 104 | −32.5 | 883 | 1.64 | 1 |
| DURI[2] | 0.9335 | 0.20 | 241 | 62 | 10 | 2,300 | 7.61 | 1 |

[1]heavy low-sulfur crude oil from Australia
[2]heavy low-sulfur crude oil from Indonesia Among the crude oils illustrated in the above table, PYR satisfies all of home fuel oil standards in terms of the properties including sulfur content, viscosity, flash point and pour point. However, DURI satisfies home fuel oil standards in terms of sulfur content, viscosity and pour point, but has a low flash point and is thus not used alone as a home fuel oil. Therefore, blending of DURI with PYR having high flash point may be preferred. In some cases, other fuel oils may be blended together.

Determination of Stability Factor

Figure 1:
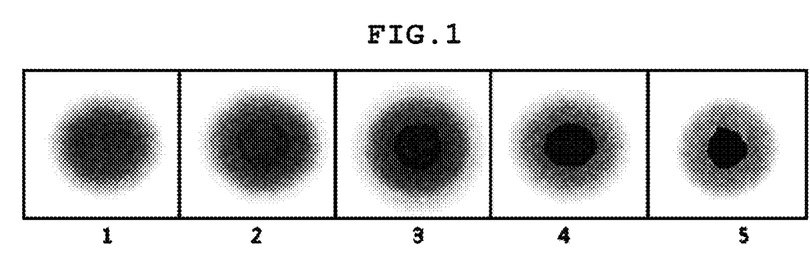
FIG. 1 illustrates standard references of SPOT testing according to ASTM D 4740-02.

In an embodiment of the present disclosure, the stability of a hydrocarbon oil blend is evaluated using a new parameter called stability factor (SF) of each of hydrocarbon oils. The stability factor may be calculated by two methods depending on the results of SPOT testing of the corresponding hydrocarbon oil. As mentioned above, SPOT testing is performed according to ASTM D 4740-02, and SPOT values are classified into five values as illustrated in FIG. 1.

(1) When the SPOT Value of Hydrocarbon Oil to be Blended is Less than 2

In an embodiment, an oil having SPOT 5, which has a high probability of causing instability due to asphaltene, is used as a reference sample, and the stability factor may be deduced by Mathematical Formula 2 below.

$$\text{Stability Factor}(a_i) = 1 \times B_i^{-1} \qquad \text{[Mathematical Formula 2]}$$

In Mathematical Formula 2, $B_i$ is the minimum amount of a hydrocarbon oil (i) to be blended with 100 g of a reference sample having SPOT 5 so as to exhibit SPOT 1.

As such, the reference sample is not fixed to specific properties so long as it fulfills SPOT 5. Since such a reference sample is an oil fraction produced in a specific reaction process during the oil refining, the properties thereof may vary depending on changes in the raw material for the corresponding process and the reaction conditions. However, when the corresponding process is stabilized and the process parameters are particularly fixed, the resulting oil may have comparatively uniform properties and may thus be used as a reference sample. When the obtained stability factor values are arranged into a database, they may be simply utilized in a stability prediction model.

In an exemplary embodiment, VRDS t-AR (vacuum residue desulfuization treated atmospheric residue) may be used upon EOR (end of run) of desulfurization of vacuum residue as a reference sample. The exemplary properties and stability thereof are shown in Table 4 below.

TABLE 4

| Classification | Properties | | | | | | | Stability | |
| --- | --- | --- | --- | --- | --- | --- | --- | --- | --- |
| | Gravity (15/4° C.) | Flash point (° C.) | Viscosity (mm²/s) | Sulfur (wt %) | Pour point (° C.) | Residual Carbon (wt %) | Asphaltene (wt %) | SPOT | HFT (wt %) |
| Max. | 0.9400 | 214 | 234 | 0.34 | 32.5 | 5.7 | 4.10 | 5 | 0.15 |
| Min. | 0.9100 | 188 | 76 | 0.27 | 2.0 | 1.7 | 1.70 | | 0.07 |

In an alternative embodiment, in some cases, an oil having SPOT 5 is not readily available. In this case, another type of oil, which may be used as the reference sample and is readily available, for example, an oil having SPOT 4, may be conveniently used. Even though an oil having SPOT 4 is used as the reference sample, the stability factor may be determined by being converted (modified) into a value when using an oil having SPOT 5, as represented by Mathematical Formula 3 below.

$$\text{Stability Factor}(a_i) = 1 \times C_i^{-1} \times 0.828 \qquad \text{[Mathematical Formula 3]}$$

In Mathematical Formula 3, $C_i$ is the minimum amount of a hydrocarbon oil (i) to be blended with 100 g of a reference sample having SPOT 4 so as to exhibit SPOT 1.

In Mathematical Formula 3, to obtain a value when using the reference sample having SPOT 5, the stability factor may be deduced by multiplying 0.828 as an empirical (experience) constant (a constant obtained through experiment).

Similarly to the aforementioned embodiment, so long as the reference sample satisfies SPOT 4, it is not fixed to specific properties. The oil having SPOT 4 with properties and stability as shown in Table 5 below may be illustratively used.

TABLE 5

| Classification | Properties | | | | | | | Stability | |
| --- | --- | --- | --- | --- | --- | --- | --- | --- | --- |
| | Gravity (15/4° C.) | Flash point (° C.) | Viscosity (mm²/s) | Sulfur (wt %) | Pour point (° C.) | Residual carbon (wt %) | Asphaltene (wt %) | SPOT | HFT (wt %) |
| Max. | 0.9350 | 210 | 230 | 0.33 | 30.0 | 5.7 | 3.90 | 4 | 0.13 |
| Min. | 0.9100 | 180 | 70 | 0.26 | 2.0 | 1.6 | 1.60 | | 0.06 |

(2) When the SPOT Value of Hydrocarbon Oil to be Blended is 2 or More

When the SPOT value of a hydrocarbon oil is 2 or more, it is difficult to reach SPOT 1 even after blending with the reference sample having SPOT 5. In this embodiment, toluene is used as a standard sample, and a stability factor may be determined by Mathematical Formula 4 below.

$$\text{Stability Factor}(a_i) = -(0.025 \times T_i \times 0.01) \quad \text{[Mathematical Formula 4]}$$

In Mathematical Formula 4, $T_i$ is the minimum amount of toluene to be blended with 100 g of the hydrocarbon oil (i) so as to exhibit SPOT 1.

Since the stability factor for the reference sample cannot be directly determined, the solubility in the reference sample is measured using toluene able to easily dissolve asphaltene and thus the stability factor is determined, after which the solubility in toluene is measured and the stability factor for the reference sample is indirectly measured, as represented by Mathematical Formula 4.

Determining (Checking) of Stability of Blend

As mentioned above, when the stability factor of each of the hydrocarbon oils to be blended is determined, the stability of the hydrocarbon oils to be blended may be determined or checked by Mathematical Formula 1 below.

$$\sum_{i=1}^{n} a_i A_i > 0 \quad \text{[Mathematical Formula 1]}$$

In Mathematical Formula 1, $a_i$ is the stability factor of the hydrocarbon oil (i) in the blend, $A_i$ is wt % of the hydrocarbon oil (i) in the blend, and n indicates the number of hydrocarbon oils in the blend and is an integer of 2 or more. In an embodiment, the number of hydrocarbon oils in the blend may be, for example, 2 to 5, and particularly 2 to 4.

As used herein, the value calculated by the Mathematical Formula as above refers to "stability factor value (SFV)". Before actual blending, the stability factor of the corresponding hydrocarbon oil is substituted into the above Mathematical Formula. When the resulting SFV is larger than 0, the blend is regarded stable. In an embodiment, two or more hydrocarbon oils may be blended depending on the composition predicted to ensure stability based on the stability prediction model.

The blend of two or more hydrocarbon oils thus prepared may represent, for example, SPOT (ASTM D 4740-02) of less than 2 (particularly, SPOT 1), and HFT (ASTM D 4870-99) of about 0.16 wt % or less. These numerical ranges are illustrative, and may vary depending on the properties of hydrocarbon oils to be blended.

The hydrocarbon oil blends thus prepared may be applied to various fields, especially fuel oils or ship oils.

A better understanding of the present invention may be obtained via the following examples which are set forth to illustrate, but are not to be construed as limiting the present invention.

Sample

Hydrocarbon oil: Heavy oil of Table 2 and crude oil of Table 3.

Reference sample: Oil having SPOT 5 of Table 6 below (VRDS t-AR; vacuum residue desulfurization treated atmospheric residue) and oil having SPOT 4 of Table 7 below.

TABLE 6

| | Properties | | | | | | Stability | |
|---|---|---|---|---|---|---|---|---|
| Gravity (15/4° C.) | Flash point (° C.) | Viscosity (mm²/s) | Sulfur (wt %) | Pour point (° C.) | Residual carbon (wt %) | Asphaltene (wt %) | SPOT | HFT (wt %) |
| 0.9100 | 188 | 76 | 0.33 | 2.0 | 3.3 | 2.10 | 5 | 0.09 |

TABLE 7

| | Properties | | | | | | Stability | |
|---|---|---|---|---|---|---|---|---|
| Gravity (15/4° C.) | Flash point (° C.) | Viscosity (mm²/s) | Sulfur (wt %) | Pour point (° C.) | Residual carbon (wt %) | Asphaltene (wt %) | SPOT | HFT (wt %) |
| 0.9189 | 208 | 150 | 0.28 | 10.0 | 3.7 | 1.93 | 4 | 0.10 |

Toluene: Extra Pure product available from DC Chemical.
Crude oil: crude oil of Table 3.

Example 1

Calculation of Stability Factor (1) Calculation of Stability Factor Using Reference Sample (Less than SPOT 2)

1) The minimum amount of a hydrocarbon oil to be blended with 100 g of a reference sample (oil having SPOT 5) to adjust the SPOT value of the blend to 1 was measured through the following procedures, and a stability factor was calculated.

The reference sample was added with the corresponding sample in a predetermined amount (an expected amount), and stored in an oven at 50° C. for 30 min, after which some of the mixed sample was taken and subjected to SPOT testing according to ASTM D4740. These procedures were repeated, as necessary. When the SPOT value of the blend arrived at 1, the amount of added hydrocarbon oil was decided as an addition amount for calculation of the stability factor.

The amount (minimum amount) of each of added hydrocarbon oils and the stability factor (SF; $a_i$) of Mathematical Formula 2 are shown in Table 8 below.

TABLE 8

| Sample | Added amount (g) | Stability factor (SF) | Note |
|---|---|---|---|
| Toluene | 40 | 0.0250 | |
| LCO | 25 | 0.0400 | |
| HCN | 35 | 0.0286 | |
| SLO | 60 | 0.0167 | |
| H/S AR | 1,900 | 0.0005 | |
| L/S AR | 1,900 | 0.0005 | |
| t-LGO | — | 0 | It has SPOT 1, but SPOT is not improved upon blending with reference sample and thus stability factor is determined to be 0 |

2) The amount (minimum amount $C_i$) of each of added hydrocarbon oils was determined in the same manner as in Procedure 1), with the exception that an oil having SPOT 4 was used as the reference sample, instead of the oil having SPOT 5. Then, $C_i^{-1}$ was determined and multiplied by an empirical constant 0.828, as represented by Mathematical Formula 3, thus calculating a stability factor ($a_i$). The results are shown in Table 9 below.

TABLE 9

| Sample | Added amount (g) | $C_i^{-1}$ | Stability Factor (SF) | Note |
|---|---|---|---|---|
| Toluene | 33 | 0.0302 | 0.0250 | |
| LCO | 21 | 0.0483 | 0.0400 | |
| HCN | 29 | 0.0345 | 0.0286 | |
| SLO | 50 | 0.0202 | 0.0167 | |
| H/S AR | 1,656 | 0.0006 | 0.0005 | |
| L/S AR | 1,656 | 0.0006 | 0.0005 | |
| t-LGO | — | 0 | 0 | It has SPOT 1, but SPOT is not improved upon blending with reference sample and thus stability factor is determined to be 0 |

As is apparent from Table 9, when the oil having SPOT 4 was used as the reference sample, the stability factor obtained by multiplying the constant 0.828 shows the same value as the stability factor of Table 8 using the oil having SPOT 5 as the reference sample. Therefore, to even when the oil having SPOT 4 is used as the reference sample, in addition to the oil having SPOT 5, the consistent SFV may be obtained for individual hydrocarbon oils.

(2) Calculation of Stability Factor Using Toluene (SPOT 2 or More)

The minimum amount of toluene to be blended with 100 g of the corresponding sample to adjust the SPOT value of the blend to 1 was measured through the following procedures, and a stability factor was calculated.

The corresponding sample was added with toluene in a predetermined amount (an expected amount), and stored in an oven at 50° C. for 30 min, after which some of the mixed sample was taken and subjected to SPOT testing according to ASTM D4740. These procedures were repeated, as necessary. When the SPOT value of the blend arrived at 1, the amount of added toluene was decided as an addition amount for calculation of the stability factor.

The amount (minimum amount) of added toluene and the stability factor (SF) are shown in Table 10 below.

TABLE 10

| Sample | Added Toluene (g) | Stability Factor (SF) |
|---|---|---|
| RHDS t-AR | 32 | −0.0080 |
| VRDS t-AR | 40 | −0.0100 |

Figure 2:
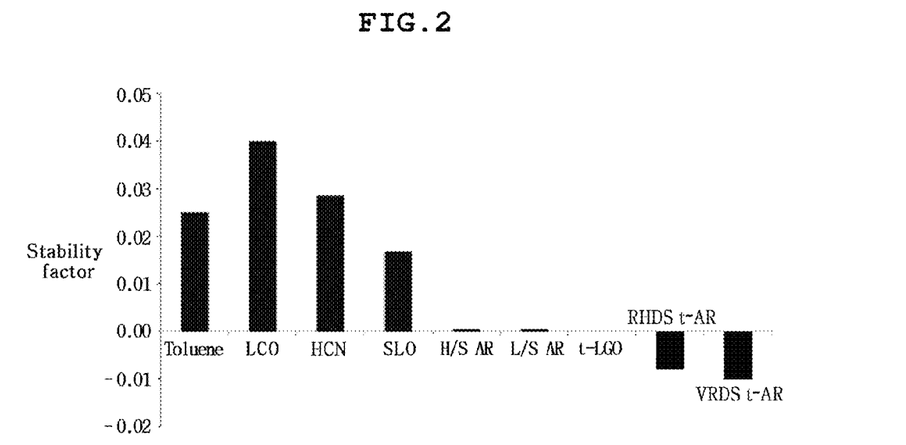
FIG. 2 illustrates a graph of stability factor values of samples measured in Example 1 according to the present disclosure.

The results of stability factor for nine samples as is apparent from Tables 9 and 10 are depicted in FIG. 2.

As depicted in this drawing, the stability factor of LCO was the highest, and the stability factor was high in the order of HCN, toluene, SLO, H/S AR (L/S AR) and t-LGO. It is supposed that, as the stability factor is higher, the oil has the properties capable of improving the stability of the blend. However, RHDS t-AR and VRDS t-AR are assumed to have a high probability of deteriorating the stability of the blend. Such results are matched with the SPOT values.

Calculation of Stability Factor Value (SFV)

The stability factor value (SFV) of the blend of three hydrocarbon oils (and toluene) selected based on the results of stability factor of Tables 9 and 10 was evaluated. To this end, the hydrocarbon oils having a high stability factor were sequentially blended and maintained in an oven at 50° C. for 30 min. The stability of the blends was measured based on the SPOT testing, thus evaluating reliability of SFV.

The blending ratio and SFV in this embodiment, and the properties and stability (SPOT) of actually prepared blends are shown in Tables 11 and 12 below.

TABLE 11

| | Blend Composition (wt %) | | | | | | | | | | |
|---|---|---|---|---|---|---|---|---|---|---|---|
| Case | LCO | HCN | SLO | t-LGO | L/S AR | H/S AR | RHDS t-AR | VRDS t-AR | Toluene | SFV | Check |
| 1 | 14.3 | 14.3 | | | | | | 71.4 | | 0.267 | >0 |
| 2 | | 14.3 | | | | | 14.3 | 71.4 | | −0.419 | <0 |
| 3 | 14.3 | | 14.3 | | | | | 71.4 | | 0.097 | >0 |
| 4 | | | 14.3 | | | 14.3 | | 71.4 | | −0.468 | <0 |
| 5 | | | | 14.3 | 14.3 | | | 71.4 | | −0.707 | <0 |
| 6 | 14.3 | | | | 14.3 | | 71.4 | | | 0.001 | >0 |
| 7 | 14.3 | | | | | 14.3 | 71.4 | | | 0.008 | >0 |
| 8 | 14.3 | | | | | | | 71.4 | 14.3 | 0.216 | >0 |
| 9 | | 14.3 | | | 71.4 | | 14.3 | | | 0.330 | >0 |
| 10 | | | 14.3 | 14.3 | | 71.4 | | | | 0.275 | >0 |
| 11 | | | | 14.3 | | 14.3 | 71.4 | | | −0.566 | <0 |

TABLE 12

| Case | Gravity (15/4° C.) | Flash point (° C.) | Viscosity (mm$^2$/s) | Sulfur (wt %) | Pour point (° C.) | SPOT |
|---|---|---|---|---|---|---|
| 1 | 0.9418 | 83 | 44 | 0.39 | 17.5 | 1 |
| 2 | 0.9277 | 83 | 77 | 0.30 | 20.0 | 5 |
| 3 | 0.9637 | 87 | 95 | 0.50 | 20.0 | 1 |
| 4 | 0.9574 | 87 | 232 | 0.91 | 22.5 | 5 |
| 5 | 0.9178 | 86 | 107 | 0.24 | 25.0 | 5 |
| 6 | 0.9290 | 116 | 49 | 0.36 | 27.5 | 1 |
| 7 | 0.9433 | 186 | 110 | 0.40 | 15.0 | 1 |
| 8 | 0.9331 | 34 | 31 | 0.34 | 17.4 | 1 |
| 9 | 0.9397 | 104 | 132 | 0.28 | 27.5 | 1 |
| 10 | 0.9764 | 106 | 239 | 2.85 | 10.0 | 1 |
| 11 | 0.9227 | 117 | 107 | 0.77 | 10.0 | 5 |

As is apparent from Tables 11 and 12, when two oils having SPOT 1 were blended with VRDS t-AR in the same amount (Case 1 to 4), SFV was represented by (+) or (−) depending on the type of oil to be blended, and the stability predicted therefrom was consistent with the actually measured stability test (SPOT test) results. Specifically, in Case 1 and 2 where the blending ratio of HCN and VRDS t-AR was fixed and a different oil was used (Case 1: LCO, Case 2: RHDS t-AR), there was an obvious difference in stability (Case 1: stable, Case 2: unstable). Also, in Case 3 and 4 where the blending ratio of SLO and VRDS t-AR was fixed and a different oil was used (Case 3: LCO, Case 4: H/S AR), stability behavior was different (Case 3: stable, Case 4: unstable).

This means that a specific oil affects the solubility of asphaltene contained in the other oil to be blended together therewith, and also that the stability of the total blend cannot be checked indiscriminately by only the properties of individual oils. Therefore, the SFV in this embodiment is very useful and effective in checking the stability of the blend. Moreover, when the criteria for determining stability as shown in this embodiment are utilized, very stable blends may be prepared despite the use of a large amount of VRDS t-AR able to easily cause instability.

Such results may also be applied to blends containing a large amount of RHDS t-AR. In Case 6, 7 and 11, when the two kinds of oils blended with RHDS t-AR (71.4 wt %) were changed (Case 6: LCO and t-LGO, Case 7: LCO and L/S AR, Case 11: t-LGO and H/S AR), different stability behaviors were exhibited (Case 6: stable, Case 7: stable, and Case 11: unstable).

In the other blend compositions (Case 8 to 10), the prediction results based on the calculated stability factor value (SFV) were also consistent with the actual blend stability results.

Example 2

Preparation of Home Fuel Oil Blend Using Crude Oil

The stability factor (SF) for two crude oils (PYR and DURI; SPOT 1) was determined using the method of Example 1, and the stability factor value (SFV) for the blend of two crude oils was measured. The results are shown in Tables 13 and 14 below.

TABLE 13

| Sample | Added Amount (g) | Stability Factor (SF) |
|---|---|---|
| PYR | 90 | 0.0111 |
| DURI | 150 | 0.0067 |

TABLE 14

| Blend composition (wt %) | | | |
|---|---|---|---|
| PYR | DURI | SFV | Check |
| 72.0 | 28.0 | 0.987 | >0 |

TABLE 15

| Gravity (15/4° C.) | Sulfur (wt %) | Viscosity (mm$^2$/s) | Flash point (° C.) | Pour point (° C.) | Nitrogen (ppm) | CCR (wt %) | SPOT |
|---|---|---|---|---|---|---|---|
| 0.9372 | 0.20 | 65 | 116 | 17.5 | 1603 | 2.74 | 1 |

As is apparent from Table 15, the blend of two crude oils may satisfy typical standards for representative properties of fuel oil (especially bunker-C) as shown in Table 16 below, and stability thereof may also become superior. Thus, upon transporting the blend, problems such as pipe clogging may not occur. In particular, the check criteria shown in this embodiment and the actual stability were consistent.

TABLE 16

| Item | Bunker-A | Bunker-B | Bunker-C |
|---|---|---|---|
| Flash point (° C.) | 60 or more | 65 or more | 70 or more |
| Pour point (° C.) | 5 or less | 10 or less | — |
| CCR (wt %) | 8 or less | 12 or less | — |
| Sulfur (wt %) | 2 or less | 3 or less | 4 or less |

To evaluate long-term storage stability, Turbiscan testing was performed according to ASTM 7061-05A. The blend had a value of 0.2 and thus exhibited superior long-term storage stability.

Figure 3A:
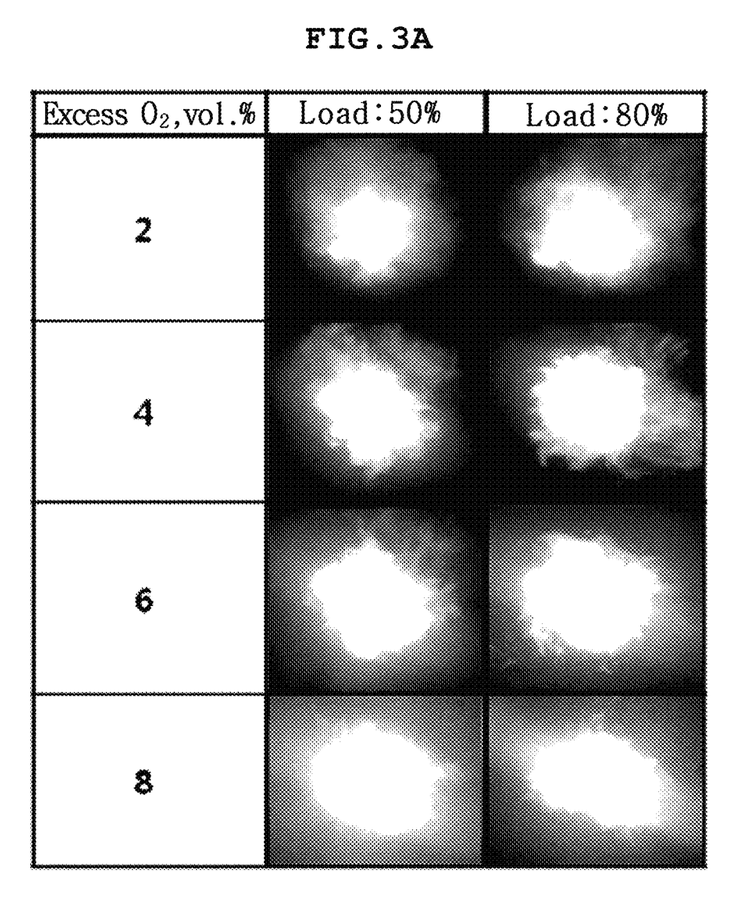
FIGS. 3a and 3b illustrate rear images and lateral images respectively of a flame showing the results of combustion testing of a home fuel oil blend (bunker-C oil satisfying the specification of sulfur content of 0.3%) in Example 2 according to the present disclosure.
Figure 3B:
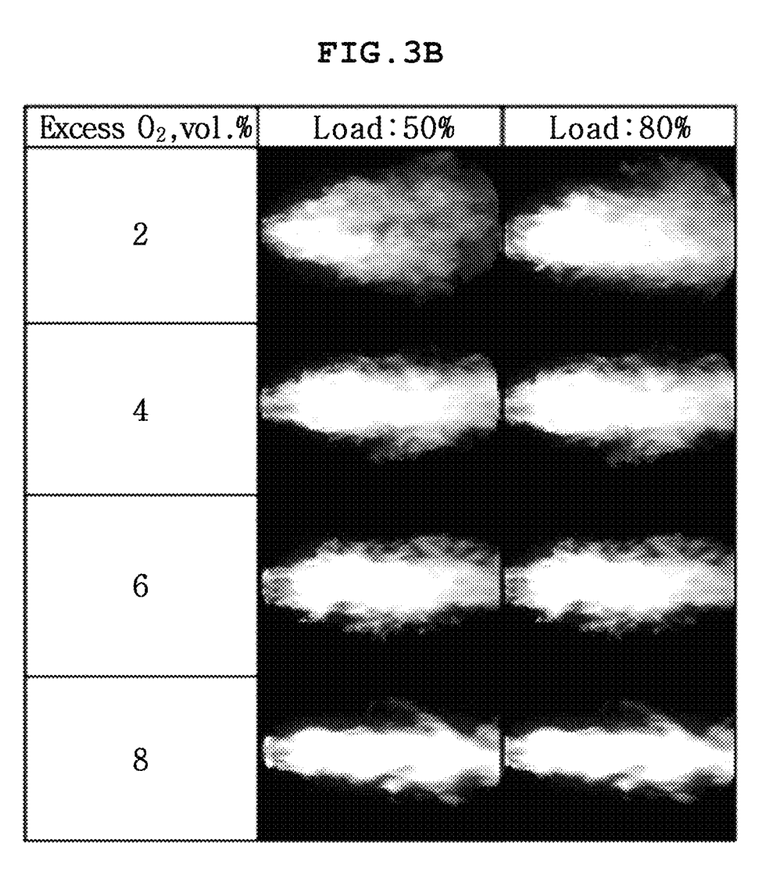

Also, combustion performance of the crude oil blend was tested using a vertical once-through heat-medium boiler (spray type: high pressure flow type, fuel temp. at inlet of burner: 115° C.) available from Hamworthy. While the amount of excess oxygen in an ignition state was changed (2 vol %, 4 vol %, 6 vol % and 8 vol %, respectively) and the load was changed (50% and 80%, respectively), the flame state was observed. The results are shown in FIGS. 3a and 3b. As shown in these drawings, there were no ignition problems.

As mentioned above, DURI crude oil had a low flash point and thus cannot be used alone as a home fuel oil, but the stable blend thereof with the other crude oil (PYR) may be applied as a home fuel oil without particular problems.

Example 3

Application of Heavy Oil Product (Blend) to Small Boiler

A plurality of hydrocarbon oils (heavy oils) used in Example 1 was blended as shown in Table 17 below, thus preparing a blend. The properties of the prepared heavy oil product (blend) are given in Table 18 below.

TABLE 17

| Classification | Blending ratio (wt %) | | | | | SFV |
|---|---|---|---|---|---|---|
| | L/S AR | t-LGO | HCN | LCO | Total | |
| Blend | 20.0 | 31.0 | 39.0 | 10.0 | 100 | 1.525 |

TABLE 18

| Classification | Properties | | | | | |
|---|---|---|---|---|---|---|
| | Gravity (15/4° C.) | Flash point (° C.) | Viscosity (mm²/s) | Sulfur (wt %) | Pour point (° C.) | SPOT |
| Blend | 0.9158 | 78 | 4.0 | 0.28 | −2.5 | 1 |

The heavy oil product (blend) thus prepared was applied to a small boiler (a burner) for greenhouses and thus ignition, flame state, and generation of soot were observed with the naked eye. As such, the boiler was an FBR burner (with a heat gun, full load: 42 L/hr).

Based on the evaluation results, (i) there were no ignition problems at night or in the dawn during the winter requiring a large amount of fuel, (ii) there were neither flame nor fire power problems compared to conventional products, and (iii) there was no soot based on the results of observation of exhaust gas in a chimney.

Example 4

Application of Heavy Oil Product (Blend) to Small Burner

A plurality of hydrocarbon oils (heavy oils) used in Example 1 were blended as shown in Table 19 below, thus preparing blends. The properties of the prepared heavy oil products (blends) are given in Table 20 below.

TABLE 19

| Classification | Blending ratio (wt %) | | | | | SFV |
|---|---|---|---|---|---|---|
| | VRDS t-AR | t-LGO | HCN | LCO | Total | |
| Blend 1 | 40.0 | 24.0 | 29.0 | 7.0 | 100 | 0.709 |
| Blend 2 | 23.0 | 34.0 | 35.0 | 8.0 | 100 | 1.091 |

TABLE 20

| Classification | Properties | | | | | |
|---|---|---|---|---|---|---|
| | Gravity (15/4° C.) | Flash point (° C.) | Viscosity (mm²/s) | Sulfur (wt %) | Pour point (° C.) | SPOT |
| Blend 1 | 0.9150 | 77 | 11.0 | 0.28 | 5.0 | 1 |
| Blend 2 | 0.9079 | 75 | 6.0 | 0.26 | −2.5 | 1 |

Each of the two heavy oil products (Blend 1: high-viscosity blend, Blend 2: low-viscosity blend) thus prepared was applied to a small burner and an ignition state or a combustion state was evaluated. As such, to evaluate heavy oil products, a burner (SHG 30M) available from Seunghwa Industry Co. was used.

Based on the evaluation results, a performance test for Blend 1 was performed at different fuel temperatures, and viscosity thereof was changed depending on changes in temperature through the preheat of the fuel. While the supply of air into the burner was adjusted together with the temperature control, the test was performed. As such, the test was conducted while adjusting the amount of excess $O_2$ (%). The results are shown in Table 21 below.

TABLE 21

| Temperature ° C. | Temperature Control | Excess $O_2$ (%) | | | | |
|---|---|---|---|---|---|---|
| | | 1 | 2 | 3 | 4 | 5 |
| 40 | Use of preheater | ○ | ○ | ○ | X | X |
| 43 | | ○ | ○ | ○ | ○ | X |
| 50 | | ○ | ○ | ○ | ○ | Δ |
| 60 | | ○ | ○ | ○ | ○ | ○ |

○: good ignition
Δ: fair ignition
X: poor ignition

As is apparent from Table 21, when Blend 1 having high viscosity was preheated to 60° C. or higher, ignition could occur even when the amount of excess $O_2$ was 5%, and there was no problem upon re-ignition.

Figure 4:
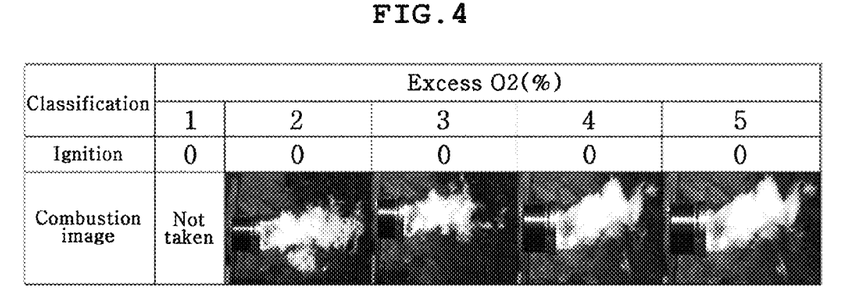
FIG. 4 illustrates the results (ignition and flame) of combustion testing of a heavy oil product (blend) of Example 4 according to the present disclosure applied to a small boiler.

On the other hand, Blend 2 having low viscosity was measured for ignition and combustion thereof. The results are shown in FIG. 4. As such, the blend was tested at room temperature (32.5° C.).

As shown in the drawing, Blend 2 could be ignited at all excess $O_2$ amounts.

Example 5

Application of Heavy Oil Product (Blend) to Ship Oil

A plurality of hydrocarbon oils (heavy oils) used in Example 1 were blended as shown in Table 22 below, thus preparing a blend. The properties of the prepared heavy oil product (blend) are given in Table 23 below.

TABLE 22

| Classification | Mixing ratio (wt %) | | | | | SFV |
|---|---|---|---|---|---|---|
| | H/S AR | t-LGO | HCN | LCD | Total | |
| Blend | 18.0 | 21.0 | 37.0 | 24.0 | 100 | 2.027 |

TABLE 23

| Classification | Properties | | | | | |
|---|---|---|---|---|---|---|
| | Gravity (15/4° C.) | Flash point (° C.) | Viscosity (mm²/s) | Sulfur (wt %) | Pour point (° C.) | SPOT |
| Blend | 0.9442 | 80 | 6.0 | 1.03 | −10.0 | 1 |

Figure 5A:
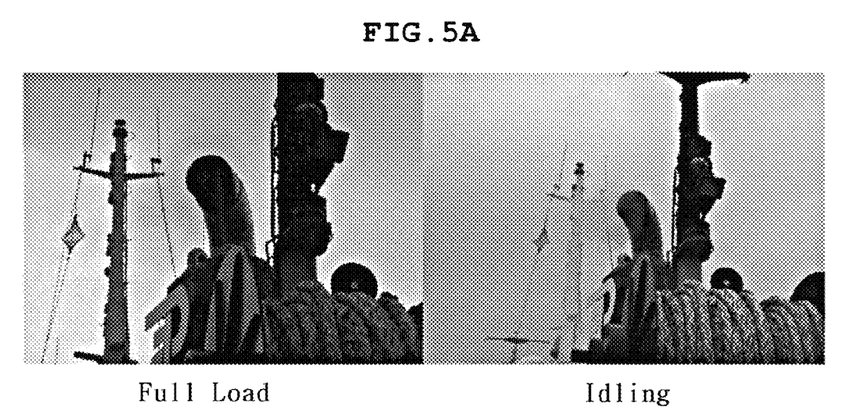
FIGS. 5a and 5b illustrate images showing the properties of exhaust gas upon full load (a maximum power state) and idling (after startup) of an conventional heavy oil product and a heavy oil product (blend) of Example 5 according to the present disclosure, which are respectively applied to a small ship engine.
Figure 5B:
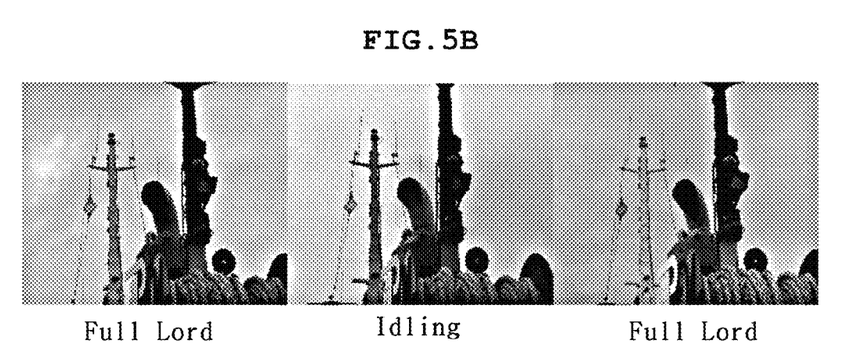

The heavy oil product (blend) thus prepared was applied as ship oil for a ship (Tugboat, 84 ton 1200PS; fuel consumption: 14 L/hr). Upon evaluation, startup capability was evaluated, and exhaust gas was observed with the naked eye upon full load (Max. power 330-340 rpm, 11 knot) and idling (Min. 200 rpm upon idling after startup). The properties of this blend were compared with those of existing ship oil illustrated in Table 24 below. The results of evaluation of characteristics of exhaust gas are shown in FIGS. 5a and 5b.

TABLE 24

| Classification | Properties | | | | | |
|---|---|---|---|---|---|---|
| | Gravity (15/4° C.) | Flash point (° C.) | Viscosity (mm²/s) | Sulfur (wt %) | Pour point (° C.) | SPOT |
| Existing ship oil | 0.9372 | 81 | 6.4 | 1.33 | −12.5 | 2 |

Based on the evaluation results, the startup capability of the blend was similar to that of the conventional ship oil.

Based on the results of combustion testing, the blend according to the present disclosure exhibited superior performance in terms of white smoke (unburned carbon upon idling), soot (or coke due to incomplete combustion) and knocking, compared to the conventional ship oil.

Accordingly, simple modifications, additions and substitutions of the present invention should also be understood as falling within the scope of the present invention, without departing from the scope and spirit of the invention as disclosed in the accompanying claims.

The invention claimed is:

1. A method of preparing a hydrocarbon blend by blending at least two hydrocarbon oils, comprising:
   determining a stability factor of each of the at least two hydrocarbon oils; and
   blending the at least two hydrocarbon oils so as to satisfy, based on the determined stability factor, a first mathematical formula, $$\sum_{i=1}^{n} a_i A_i > 0$$

wherein $a_i$ is a stability factor of a hydrocarbon oil (i) in the blend, $A_i$ is wt % of the hydrocarbon oil (i) in the blend, and n indicates a number of hydrocarbon oils in the blend and is an integer of 2 or more,
   (a) when a SPOT value of a hydrocarbon oil according to ASTM D 4740-02 is less than 2, the stability factor is determined by a second mathematical formula, Stability Factor$(a_i) = 1 \times B_i^{-1}$ wherein $B_i$ is a minimum amount of the hydrocarbon oil (i) to be blended with 100 g of a reference sample having SPOT 5 so as to exhibit SPOT 1, and
   (b) when a SPOT value of a hydrocarbon oil according to ASTM D 4740-02 is 2 or more, the stability factor is determined by a third mathematical formula, Stability Factor$(a_i) = -(0.025 \times T_i \times 0.01)$ wherein $T_i$ is a minimum amount of toluene to be blended with 100 g of the hydrocarbon oil (i) so as to exhibit SPOT 1.

2. A method of preparing a hydrocarbon blend by blending at least two hydrocarbon oils, comprising:
   determining a stability factor of each of the at least two hydrocarbon oils; and
   blending the at least two hydrocarbon oils so as to satisfy, based on the determined stability factor, a first mathematical formula, $$\sum_{i=1}^{n} a_i A_i > 0$$

wherein $a_i$ is a stability factor of a hydrocarbon oil (i) in the blend, $A_i$ is wt % of the hydrocarbon oil (i) in the blend, and n indicates a number of hydrocarbon oils in the blend and is an integer of 2 or more,
   (a) when a SPOT value of a hydrocarbon oil according to ASTM D 4740-02 is less than 2, the stability factor is determined by a second mathematical formula, Stability Factor$(a_i) = 1 \times C_i^{-1} \times 0.828$ wherein $C_i$ is a minimum amount of the hydrocarbon oil (i) to be blended with 100 g of a reference sample having SPOT 4 so as to exhibit SPOT 1, and
   (b) when a SPOT value of a hydrocarbon oil according to ASTM D 4740-02 is 2 or more, the stability factor is determined by a third mathematical formula, Stability Factor$(a_i) = -(0.025 \times T_i \times 0.01)$ wherein $T_i$ is a minimum amount of toluene to be blended with 100 g of the hydrocarbon oil (i) so as to exhibit SPOT 1.

3. The method of claim 1, wherein the hydrocarbon oils comprise crude oils, heavy oils having a gravity of 0.8 to 1.2 or mixtures thereof.

4. The method of claim 1, wherein the hydrocarbon oils have an asphaltene content of 15 wt % or less.

5. The method of claim 1, wherein the hydrocarbon oils have a sulfur content (ASTM D4294) of 5 wt % or less, a viscosity (ASTM D445/ASTM D2270) of 1 to 1500 mm²/s, a flash point (ASTM D92) of 30° C. or more, and a pour point (ASTM D97) of 40° C. or less.

6. The method of claim 5, wherein the hydrocarbon oils have a nitrogen content of 5000 ppm or less and CCR (Conradson Carbon Residue) of 15 wt % or less.

7. The method of claim 1, wherein the hydrocarbon oils are selected from the group consisting of LCO (light cycle oil), HCN (heavy catalytic cracked naphtha), SLO (slurry oil), H/S AR (high sulfur atmospheric residue), L/S AR (low sulfur atmospheric residue), t-LGO (treated light gas oil), RHDS t-AR (residue hydrodesulfurization treated atmospheric residue) and VRDS t-AR (vacuum residue desulfurization treated atmospheric residue).

8. The method of claim 1, wherein n is 2 to 5.

9. A method of preparing a hydrocarbon blend by blending at least two hydrocarbon oils, comprising:
   determining a stability factor of each of the at least two hydrocarbon oils to be blended; and
   determining stability depending on whether the blend of the hydrocarbon oils satisfies, based on the determined stability factor,
   a first mathematical formula, $$\sum_{i=1}^{n} a_i A_i > 0$$

wherein $a_i$ is a stability factor of a hydrocarbon oil (i) in the blend, $A_i$ is wt % of the hydrocarbon oil (i) in the blend, and n indicates a number of hydrocarbon oils in the blend and is an integer of 2 or more, (a) when a SPOT value of a hydrocarbon oil according to ASTM D 4740-02 is less than 2, the stability factor is determined by a second mathematical formula, $$\text{Stability Factor}(a_i) = 1 \times B_i^{-1} \qquad 5$$

wherein $B_i$ is a minimum amount of the hydrocarbon oil (i) to be blended with 100 g of a reference sample having SPOT 5 so as to exhibit SPOT 1, and (b) when a SPOT value of a hydrocarbon oil according to ASTM D 4740-02 is 2 or more, the stability factor is determined by a third mathematical formula, $$\text{Stability Factor}(a_i) = -(0.025 \times T_i \times 0.01)$$

wherein $T_i$ is a minimum amount of toluene to be blended with 100 g of the hydrocarbon oil (i) so as to exhibit SPOT 1, and wherein $C_i$ is a minimum amount of the hydrocarbon oil (i) to be blended with 100 g of a reference sample having SPOT 4 so as to exhibit SPOT 1, and (b) when a SPOT value of a hydrocarbon oil according to ASTM D 4740-02 is 2 or more, the stability factor is determined by a third mathematical formula, $$\text{Stability Factor}(a_i) = -(0.025 \times T_i \times 0.01)$$

wherein $T_i$ is a minimum amount of toluene to be blended with 100 g of the hydrocarbon oil (i) so as to exhibit SPOT 1, and (c) blending the at least two hydrocarbon oils so as to satisfy the first mathematical formula based on the determined stability factor.

11. The method of claim 9, further comprising forming a database of the stability factor of each of the at least two hydrocarbon oils, before checking the stability.

12. The method of claim 9, wherein the reference sample having SPOT 5 has the following properties

| | Properties | | | | | | | Stability | |
|---|---|---|---|---|---|---|---|---|---|
| Classification | Gravity (15/4° C.) | Flash point (° C.) | Viscosity (mm²/s) | Sulfur (wt %) | Pour point (° C.) | Residual Carbon (wt %) | Asphaltene (wt %) | SPOT | HFT (wt %) |
| Max. | 0.9400 | 214 | 234 | 0.34 | 32.5 | 5.7 | 4.10 | 5 | 0.15 |
| Min. | 0.9100 | 188 | 76 | 0.27 | 2.0 | 1.7 | 1.70 | | 0.07. |

13. The method of claim 10, wherein the reference sample having SPOT 4 has the following properties

| | Properties | | | | | | | Stability | |
|---|---|---|---|---|---|---|---|---|---|
| Classification | Gravity (15/4° C.) | Flash point (° C.) | Viscosity (mm²/s) | Sulfur (wt %) | Pour point (° C.) | Residual Carbon (wt %) | Asphaltene (wt %) | SPOT | HFT (wt %) |
| Max. | 0.9350 | 210 | 230 | 0.33 | 30.0 | 5.7 | 3.90 | 4 | 0.13 |
| Min. | 0.9100 | 180 | 70 | 0.26 | 2.0 | 1.6 | 1.60 | | 0.06. |

(c) blending the at least two hydrocarbon oils so as to satisfy the first mathematical formula based on the determined stability factor.

10. A method of preparing a hydrocarbon blend by blending at least two hydrocarbon oils, comprising:
determining a stability factor of each of the at least two hydrocarbon oils to be blended; and
determining stability depending on whether the blend of the hydrocarbon oils satisfies, based on the determined stability factor,
a first mathematical formula, $$\sum_{i=1}^{n} a_i A_i > 0$$

wherein $a_i$ is a stability factor of a hydrocarbon oil (i) in the blend, $A_i$ is wt % of the hydrocarbon oil (i) in the blend, and n indicates a number of hydrocarbon oils in the blend and is an integer of 2 or more, (a) when a SPOT value of a hydrocarbon oil according to ASTM D 4740-02 is less than 2, the stability factor is determined by a second mathematical formula, $$\text{Stability Factor}(a_i) = 1 \times C_i^{-1} \times 0.828$$

14. The method of claim 10, further comprising forming a database of the stability factor of each of the at least two hydrocarbon oils, before checking the stability.

15. The method of claim 2, wherein the hydrocarbon oils comprise crude oils, heavy oils having a gravity of 0.8 to 1.2 or mixtures thereof.

16. The method of claim 2, wherein the hydrocarbon oils have an asphaltene content of 15 wt % or less.

17. The method of claim 2, wherein the hydrocarbon oils have a sulfur content (ASTM D4294) of 5 wt % or less, a viscosity (ASTM D445/ASTM D2270) of 1 to 1500 mm²/s, a flash point (ASTM D92) of 30° C. or more, and a pour point (ASTM D97) of 40° C. or less.

18. The method of claim 17, wherein the hydrocarbon oils have a nitrogen content of 5000 ppm or less and CCR (Conradson Carbon Residue) of 15 wt % or less.

19. The method of claim 2, wherein the hydrocarbon oils are selected from the group consisting of LCO (light cycle oil), HCN (heavy catalytic cracked naphtha), SLO (slurry oil), H/S AR (high sulfur atmospheric residue), L/S AR (low sulfur atmospheric residue), t-LGO (treated light gas oil), RHDS t-AR (residue hydrodesulfurization treated atmospheric residue) and VRDS t-AR (vacuum residue desulfurization treated atmospheric residue).

20. The method of claim 2, wherein n is 2 to 5.

* * * * *